(12) United States Patent
George et al.

(10) Patent No.: US 8,666,676 B2
(45) Date of Patent: Mar. 4, 2014

US008666676B2

(54) METHOD AND SYSTEM FOR ANALYZING CALCIUM TRANSIENTS IN COUPLED CELLS

(75) Inventors: Christopher Hugh George, Cardiff (GB); Steven Roger Barberini-Jammaers, Cardiff (GB); Nicole Cherie Silvester, Cardiff (GB)

(73) Assignee: University College Cardiff Consultants Limited, Cardiff (GB)

( * ) Notice: Subject to any disclaimer, the term of this patent is extended or adjusted under 35 U.S.C. 154(b) by 31 days.

(21) Appl. No.: 13/304,962

(22) Filed: Nov. 28, 2011

(65) Prior Publication Data

US 2012/0109532 A1 May 3, 2012

Related U.S. Application Data

(63) Continuation-in-part of application No. PCT/GB2010/001044, filed on May 26, 2010.

(30) Foreign Application Priority Data

May 27, 2009 (GB) .................................. 0909064.8

(51) Int. Cl.
  *G06F 19/10* (2011.01)
  *G06K 9/00* (2006.01)
(52) U.S. Cl.
  USPC .............................. 702/19; 382/128; 382/133
(58) Field of Classification Search
  None
  See application file for complete search history.

(56) References Cited

U.S. PATENT DOCUMENTS

| | | | |
|---|---|---|---|
| 6,514,709 B1 * | 2/2003 | Grant et al. | .................... 435/7.1 |
| 2005/0037436 A1 | 2/2005 | Samson-Himmelstjerna et al. | |
| 2006/0110778 A1 | 5/2006 | Adorante et al. | |

FOREIGN PATENT DOCUMENTS

WO   WO2008155778 A2   12/2008

OTHER PUBLICATIONS

Demuro et al. Journal of Biomedical Optics (2005) vol. 10(1):1-8.*
George et al. Current Pharmaceutical Design (2007) vol. 13:3195-3211.*
Sasaki et al. Journal of Neurophysiology (2008) vol. 100:1668-1676.*
Chen et al. Biophysical Journal (2006) vol. 90:2534-2547.*
Simpson Methods in Mol. Biol. (2006) vol. 312:3-26.*
Mukamel et al. Neuron (Sep. 24, 2009) vol. 63:747-760.*
Picht et al. Am. Journal of Cell Physiol. (2007) vol. 293:C1073-C1081.*
Claycomb PNAS (1998) vol. 95:2979-2894.*
Robert et al. The EMBO Journal (2001) vol. 20:4998-5007.*
Angelo Demuro, et al.; "Imaginig single-channel calcium microdomains"; Elsevier; Cell Calcium, vol. 40, (2006); pp. 413-422.
Shi-Qiang Wang, et al.; "Imaging Microdomain Ca2+ in Muscle Cells"; Circulation Research—Journal of the American Heart Association; vol. 2004, No. 4, Apr. 30, 2004. pp. 1011-1022.
Jianwei Shuai, et al.; "Optical single-channel recording by imaging Ca2+ flux through individual ion channels theoretical considerations and limits to resolution", Elsevier, Cell Calcium, vol. 37 (2005), pp. 283-299.

* cited by examiner

*Primary Examiner* — Lori A Clow
(74) *Attorney, Agent, or Firm* — King & Schickli, PLLC

(57) ABSTRACT

A system and method are provided for measuring dynamic phenomena in a biological, chemical or physical sample, including the measurement of $Ca^{2+}$ transients in a living system. The system and method include measuring dynamic phenomena in an in vitro cardiac cell culture system. Computing system environments and computing systems for implementing the method are provided.

34 Claims, 14 Drawing Sheets default thresholds
peak = 2
valley = 2 adjusted thresholds
peak = 3
valley = 3 more adjustment
peak = 4
valley = 4
all peaks and valleys detected

Figure 12 A
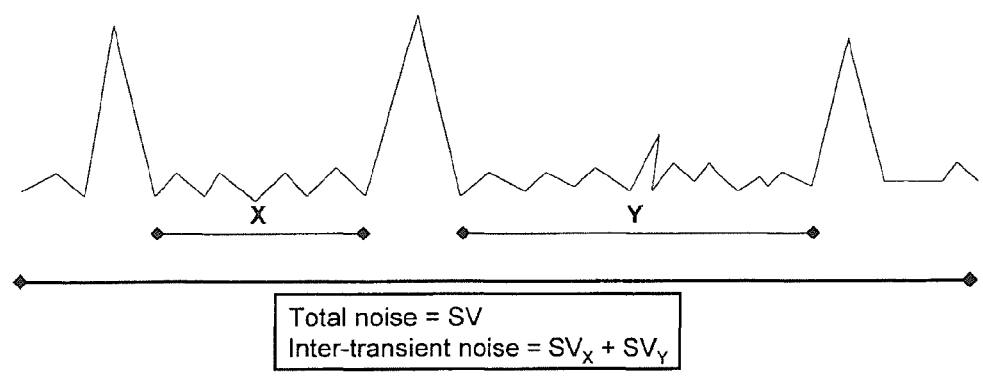
Figure 12 B
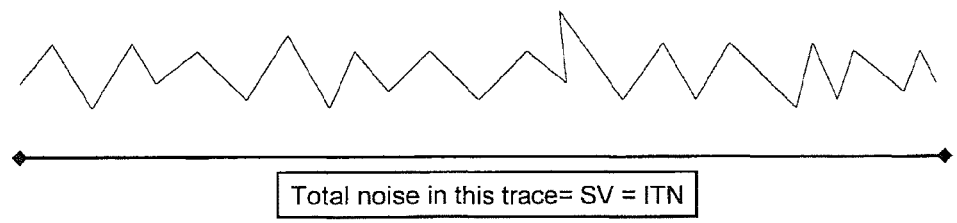
Figure 12

METHOD AND SYSTEM FOR ANALYZING CALCIUM TRANSIENTS IN COUPLED CELLS

This application is a continuation-in-part of PCT/GB2010/001044 filed on May 26, 2010, which in turn claims priority from British Patent Application Ser. No. 0909064.8 filed on May 27, 2009, the disclosures of which are incorporated herein by reference in their entirety.

FIELD OF THE INVENTION

The present invention relates to a system and method for analysing dynamic phenomena, for example biological, chemical or physical phenomena that generate data obtained in time, in particular biological processes and, more particularly still, $Ca^{2+}$ transients in biological tissue such as muscle tissue, especially, but not exclusively, heart tissue.

BACKGROUND TO THE INVENTION

There are many measurements of dynamic phenomena which generate data obtained in time, for example, a data trace of a varying measured quantity versus time and comprising a plurality of peaks. Where the peaks of the data trace represent transient events in the dynamic phenomena, analysis of the data trace typically focuses on an analysis of the peaks of the data trace, which represent transient events. This can have the advantage of reducing the volume of data undergoing detailed analysis, with an associated increase in the speed of data analysis. However, there is a risk in this approach of the data analysis not revealing a complete picture of the dynamic phenomena.

Therefore, there is a need for a quick and reliable system and method for analysing such dynamic phenomena, efficiently and accurately, so as to generate a meaningful set of parameters representing a more complete picture of the dynamic phenomena. The set of parameters can then be interpreted to obtain a holistic view of the dynamic phenomena.

SUMMARY OF THE INVENTION

According to a first aspect of the present invention there is provided a system for analysing dynamic phenomena, comprising: memory means for storing a data trace for a least one region of interest (ROI) making up a measured field of view of the dynamic phenomena, wherein the data trace represents variations in a measured parameter versus time; means for investigating the data trace, for the or each ROI, to identify the sections of the data trace comprising peaks in the trace which correspond to a transient event in the dynamic phenomena; means for selecting ROIs comprising at least one transient peak as included ROIs; and means for analysing the sections of the data trace which do not comprise transient peaks to generate a first set of parameters representing inter-transient noise for the or each included ROI. The dynamic phenomena may be a measurable dynamic phenomena derived from a sample, such as an isolated sample, in particular an isolated biological, chemical or physical sample.

The dynamic phenomena may be a biological, chemical or physical phenomena that can be measured to generate data in time, in particular a biological phenomena with a phenotypic end point. In biological systems the transient peaks may represent oscillations, whereas the inter-transient noise may represent events which may nevertheless be of interest. The measured field of view may be a field of view split into a grid of regions of interest (ROIs) such as a selected cell or a selected group of cells. The trace data may comprise a set of data points representing the measured parameter over time at a predetermined sampling rate. The measured parameter may be fluorescence intensity and may, for example, be fluorescence intensity generated from fluorescent $Ca^{2+}$ probe studies. In this case a transient may represent an event comprising $Ca^{2+}$ release, followed by $Ca^{2+}$ sequestration. In an exemplary embodiment of the invention the data trace represents calcium fluctuations in muscle tissue and most preferably heart muscle tissue in the form of, at the least, a collection of cells coupled to provide a functional syncytium. Most ideally still, said collection of cells comprises a monolayer which, ideally, is provided by culturing cardiac cells at a density of between approximately 500-1000 cells/mm².

The system may comprise means for analysing the data trace for the, or each, ROI to generate a second set of parameters representing the data trace for that ROI. The sets of parameters may each include a measure of signal variability. Thus, the system according to the present invention generates data for all of the ROIs relating to the complete data trace. This can provide an insight to a user as to why some ROIs in the field of view include a transient event, whereas others do not. The system may additionally comprise means for analysing the transient peaks to generate a third set of parameters representing transient peaks for the, or each, included ROI. Thus, the system according to the present invention generates data for each ROI relating to the transient events in that ROI. This allows the user to analyse what happens specifically to each transient and, with the separate analysis of the inter-transient noise, can enable the user to ascertain if there is any link between the inter-transient noise occurring before and after the transient and any of the transient parameters. This provides a more complete analysis of the dynamic phenomena. The system may additionally comprise means for outputting parameters for the, or each, included ROI separately.

The system may additionally comprise means for generating: a set of parameters for the field of view representing inter-transient noise based on the first set of parameters; and a set of parameters for the field of view representing transient peaks based on the third set of parameters. In addition, the system may comprise means for generating: a set of parameters for the field of view representing the data traces for included ROIs based on the second set of parameters; a set of parameters for the field of view representing the data traces for the excluded ROIs based on the second set of parameters; and a set of parameters for the field of view representing the data traces for all the ROIs in the field of view based on the second set of parameters. Therefore, a user of the system may be provided with sets of parameters (first, second and third) for the included ROIs separately as well as sets of parameters representative of the field of view in relation to the data traces of included ROIs only, the data traces of excluded ROIs only, as well as the data traces of all the ROIs. This enables a user to ascertain overall differences between included and excluded ROIs.

The set of parameters for the field of view representing transient peaks may include a measure of the synchrony between the transient peaks across the field of view based on the third set of parameters for the included ROIs. In this case, the measure of synchrony may be calculated by calculating an index that determines the total possible number of synchronised transient peaks across the field of view when compared with the actual number of synchronised transient peaks across the field of view.

The system may additionally comprise means for displaying the data trace for the or each ROI while the data trace for that ROI is investigated to identify the sections of the data trace comprising peaks in the trace which correspond to a transient event in the dynamic phenomena. Thus, the method enables the separate investigation of trace data for the different ROIs, in particular while that ROI is displayed for visual observation by the user. This enables the user to intervene should peaks representing transient events not be properly selected.

The system according to the first aspect of the present invention may perform a different analysis of the excluded ROIs as compared to the analysis of the ROIs in the included set. The analysis of the excluded ROIs may generate fewer parameters than the analysis of the included ROIs. This separates analysis of the data traces in which transient peaks occur from those in which no transient peaks occur and so allows these two types of behaviour of the dynamic phenomena to be analysed separately and then considered together by the user. In addition the including or excluding ROIs from the set of selected ROIs increases the speed of analysis for any dynamic phenomena which is not oscillatory in nature, for example, in the biological context, any experiments relating solely to non-contracting/non-beating cells. It also enables ROIs where it is not possible to discriminate between transient peaks and noise to be excluded so that they do not skew a calculation.

It is preferred that at least the signal variability (SV) is calculated for the data trace of all of the ROIs and for the inter-transient sections of the included ROIs. In particular the parameter (SV/mean of measured parameter) may be calculated for the data trace for all of the ROIs and for the inter-transient sections of each included ROI. This has been found to be very valuable in decoding dynamic systems. The signal variability may be calculated as the sum of the value differences between consecutive data points of the appropriate inter-transient portion (or the entire) data trace.

$$SV = \sum_{n=1}^{n=k-1} |(x_{n+1} - x_n)|$$

The above formula represents a mathematic description of SV for a set of k intensity values; $x_1, x_2, x_3 \ldots x_n$.

FIG. 14 shows published data of how the SV for inter-transient noise (ITN) can be used as an index of likely hazard. As SV increases, when measured at the cytoplasmic or nuclear level, cell death also increases. Further, the examples shown in FIG. 13 include ITN's gross elevation in response to a known arrhythmogen (ouabain) and also its perturbation in response to known (and clinically licensed) anti-arrhythmic drugs (designated class I-IV using the Vaughan-Williams classification of anti-arrrhythmic drugs).

The means for investigating the data trace to select peaks may comprise: means for identifying potential peak points comprising: means for assessing the slope between each data point of the trace to determine whether it is positive or negative; and means for identifying a data point as a potential peak point if it is preceded by a positive slope and followed by a negative slope. Also, the means for investigating the data trace to select peaks may comprise: means for identifying potential valley points comprising: means for assessing the slope between each data point of the trace to determine whether it is positive or negative; and means for identifying a data point as a potential valley point if it is preceded by a negative slope and followed by a positive slope. This provides an initial selection of potential peak and valley data points, which can be investigated further to identify those data points which correspond to peaks representing transient events.

The means for investigating the data trace to select peaks, once the potential peak and valley points have been determined as described above, may comprise an auto-detect model additionally comprising: means for calculating a first threshold based on the mean value of the measured parameter for the potential valley points; and means for discarding potential peak points which are below the first threshold. Then it may comprise means for discarding potential valley points which do not have a potential peak point before it or after it. Then it may comprise: means for generating a second threshold based on the mean of the measured parameter for the potential valley points; and means for discarding potential valley points which are above the second threshold. Then it may comprise means for designating a plurality of adjacent peak points as representing a potential peak. Then it may comprise means for discarding potential peaks which represent merged transient peaks. Then it may comprise means for counting the number of potential peaks in the trace and where there are more than a predetermined number of potential peaks; means for removing potential peaks that represent background noise until the standard deviation among the potential peaks is reduced to a predetermined level; and otherwise not removing any potential peaks. Then it may comprise means for: discarding potential valleys which do not have a potential peak point before it or after it; and means for discarding potential peaks which do not have a potential valley before it or after it. This auto-detect model can accurately and reliably identify peaks corresponding to transient events for many data traces.

The means for investigating the data trace to select peaks, may comprise means for designating a plurality of adjacent peak points as representing a potential peak. Then it may include: means for discarding potential peaks which represent merged transient peaks. In particular, peaks which represent merged transient peaks may be discarded for the purposes of analysing the peaks representing the transient events to generate the third set of parameters for the transient peaks for that ROI. However, the plurality of peaks which represent merged transient peaks may be identified for the purposes of calculating synchrony. Thus, the system enables marking of incomplete transient peaks, because merged transient peaks represent transient peaks that run together, i.e. one hasn't finished before the next one starts (generally due to the sampling rate). However, it is also common to get 'merged' peaks that do not resolve as single entities because of cellular fibrillation. This is not due to sampling rate but is a cellular characteristic (particularly if investigating anti-fibrillation therapies).

Missing the incomplete transient peaks can negatively impact rate and synchrony calculations. However, merged transient peaks have characteristics different from individual transient peaks Merged transient peaks do not adhere to the parametric guidelines of what a constitutes a transient and so better results are achieved for transient specific parameters if merged transient peaks are discarded from the generation of the third set of parameters for the transient peaks for each ROI. This significantly improves the results achieved according to the system according to the first aspect of the present invention because, where the sampling rate is relatively low, there can be a large number of merged transient peaks in the trace data.

The means for investigating the data trace to select peaks, once the potential peak and valley points have been determined as described above, may comprise a threshold-detect model additionally comprising: means for selecting a peak cut off threshold; means for selecting a valley cut off threshold; discarding potential peak points below the peak cut off threshold; means for discarding potential valley points above the valley cut off threshold; and means for discarding potential valley points which do not have a peak point before it or after it. In particular, the peak and valley cut off thresholds may be selected by a user on observing the trace data.

In addition or alternatively, investigating the data trace to select any transient peaks in the trace may be done, at least partially, by a user observing the trace data.

The memory means, the means for investigating, the means for selecting and the means for analysing may comprise a computing device running a computer programme. In this case, the means for displaying may comprise a display screen operatively connected to the computing device. In addition, the system may additionally comprise a user interface via which a user can interact with the system.

According to a second aspect of the present invention, there is provided a method for analysing an isolated sample generating a measurable dynamic phenomena, comprising the steps of: storing a data trace for a least one region of interest (ROI) making up a measured field of view of the sample, wherein the data trace represents variations in a measured parameter of the dynamic phenomena versus time; investigating the data trace, for the or each ROI, to identify the sections of the data trace comprising peaks in the trace which correspond to a transient event in the dynamic phenomena; selecting ROIs comprising at least one transient peak as included ROIs; and analysing the sections of the data trace which do not comprise transient peaks to generate a first set of parameters representing inter-transient noise for the or each included ROI. The isolated sample may be a biological, chemical or physical sample.

The dynamic phenomena is as previously herein describes.

The method is, advantageously, used to screen drugs in order to determine their effect on a selected type of tissue, ideally, cardiac tissue. In this instance a data trace for a functional syncytium can be compared before and after exposure to a test drug in order to capture and/or determine the effect of the test drug on the tissue. For example, a data trace can be used or analysed to show how or whether a test drug affects the synchronous beating of the tissue, the strength of contraction, the rate of contraction, a propensity towards fibrillation, or even arrest. Most commonly, a determination of the pro- or anti-arrhythmic consequence of a drug under test is assessed. However, the Ca2+ 'fingerprinting' that the system affords can also be used as an overall predictor of cellular fate. We have published the close correlation between cardiac cell viability and elevated SV. It is feasible that a drug that has negligible or benign effects on intercellular synchrony may elevate SV (or ITN) in individual cells and thus be potentially hazardous. Furthermore, regions of interest (ROIs) corresponding to subcellular compartments of interest (e.g. cytoplasm, nucleus) may be specifically selected to examine cellular Ca2+ fluxes in discrete cellular environments. See FIG. 14.

As illustrated in the FIG. 13, we convert 'raw' numerical output into a conventional 'heat map' that visually displays the parametric changes in response to pharmacologic modulation of the system. In FIG. 13 we have used a known arrhythmogenic perturbant (the cardiac glycoside, ouabain) to illustrate that the dose-dependent ablation of synchrony is linked to gross disruption of numerous Ca2+ handling parameters. Notably, the ITN is profoundly affected and strongly supports our use of this parameter in determining the likely beneficial or hazardous nature of pharmacologies under test.

FIG. 13 also includes data obtained from the system relating to known (clinically licensed) anti-arrhythmic drugs. FIG. 13 shows that the restoration of intercellular synchrony is linked to the suppression of ITN. It is well established that anti-arrhythmic pharmacologies may, under some circumstances, have remarkable pro-arrhythmic properties and the methods above show quite clearly the precise perturbations in Ca2+ handling evoked by higher dose class IV anti-arrhythmic (verapamil, 1-10 uM).

The method may additionally comprise the step of analysing the data trace for the, or each, ROI to generate a second set of parameters representing the data trace for that ROI. The sets of parameters may each include a measure of signal variability. The method may additionally comprise the step of analysing the transient peaks to generate a third set of parameters representing transient peaks for the, or each, included ROI. The method may additionally comprise the step of outputting parameters for the, or each, included ROI separately. Additionally, the method may comprise the steps of generating: a set of parameters for the field of view representing inter-transient noise based on the first set of parameters; and a set of parameters for the field of view representing transient peaks based on the third set of parameters. Also, the method may additionally comprise the steps of generating: a set of parameters for the field of view representing the data traces for included ROIs based on the second set of parameters; a set of parameters for the field of interest representing the data traces for the excluded ROIs based on the second set of parameters; and a set of parameters for the field of view representing the data traces for all the ROIs in the field of view based on the second set of parameters.

According to an aspect of the invention there is provided the use of a system according to the invention wherein the dynamic phenomena is derived from an isolated biological sample.

In a preferred embodiment of the invention the biological sample comprises isolated eukaryotic cells; preferably mammalian cells and, more particularly muscle cells, especially favoured are heart muscled cells, ideally, in the form of a functionally coupled monolayer.

In an alternative preferred embodiment of the invention said biological sample comprises prokaryotic cells; preferably bacterial cells.

In a further preferred embodiment of the invention cells are contacted with at least one agent wherein said agent induces a change in the measured dynamic phenomena and is compared to a control sample not contacted with the agent.

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

BRIEF DESCRIPTION OF THE DRAWINGS

Various aspects of the teachings of the present invention, and arrangements embodying those teachings, will hereafter be described by way of illustrative example with reference to the accompanying drawings, in which:

FIG. 12 shows a data trace and the corresponding calculation of ITN in a ROI comprising a dynamic phenomena of interest (a) and a ROI where no such phenomena exists (b);

DETAILED DESCRIPTION OF PREFERRED EMBODIMENTS

The invention relates to method and system for analysing dynamic phenomena and is referred to herein as SALVO. SALVO is a multi-parametric analytical system and method that quantifies synchrony, amplitude, length, variability and oscillatory behaviour of biological (and other) systems. It calculates the magnitude of signal flux using an index of signal variability and places it in the context of dynamic spatiotemporal events in biological processes. It is able to decode the temporal resolution of biological processes. It is especially useful in decoding oscillatory systems.

SALVO can be applied to morphological assessments at the cellular level, for example, fluctuations in nuclear size, with time, at the organ level, for example, heart contractions and rates of liver enzyme secretion. It is particularly useful for recording fluctuations of biological phenomena with a phenotypic end point.

Figure 14:
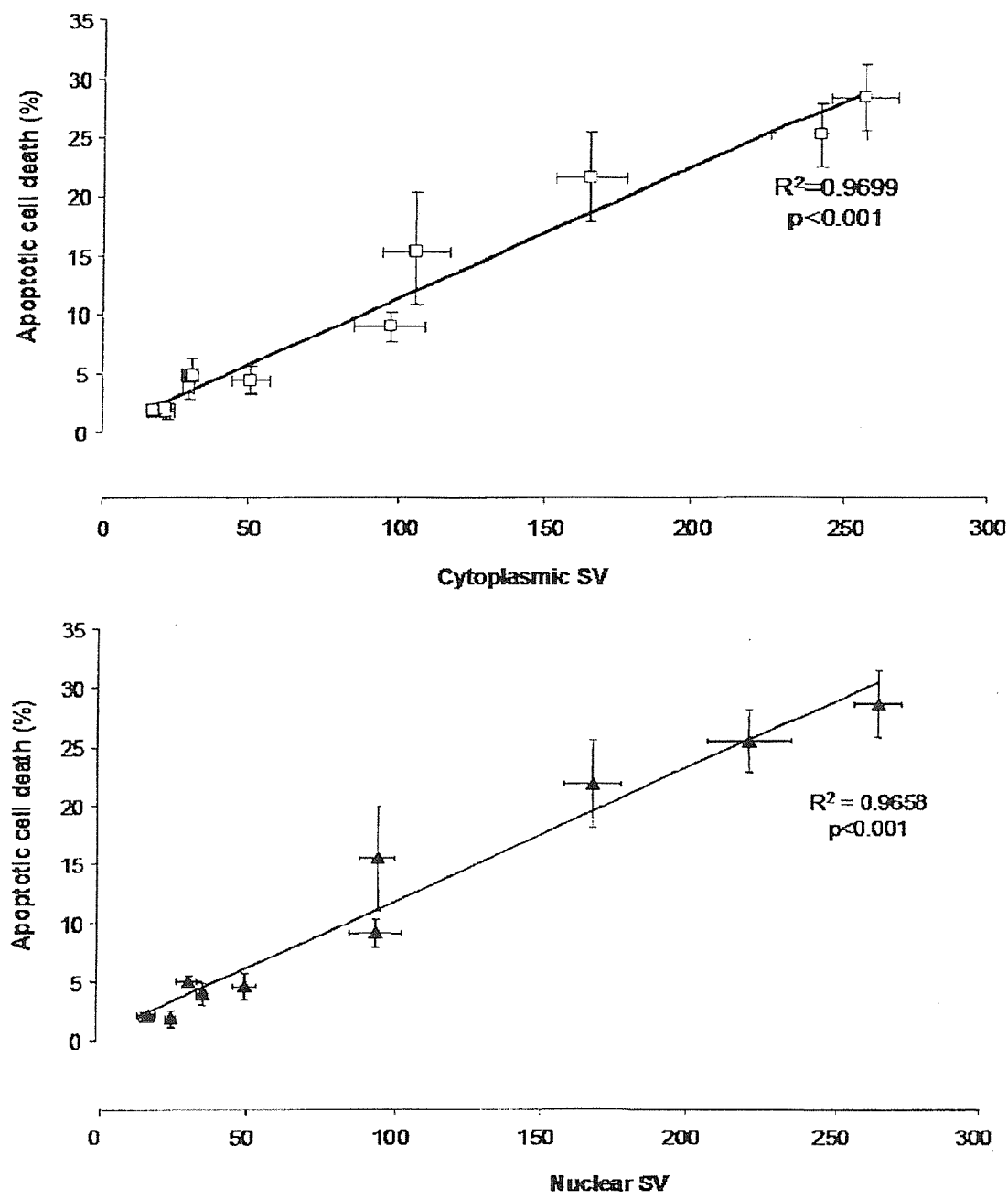
FIG. 14 is a graph of cell death v cytoplasmic and nuclear SV in cardiac tissue.

In one example SALVO has been applied to analyse $Ca^{2+}$ transient periodicity, rates of release and intercellular $Ca^{2+}$ synchrony. SALVO is able to decode the $Ca^{2+}$ handling basis of cellular rhythmicity, synchronicity and contractility in cardiac monolayers in vitro. Ideally, the analysis is applied to signals generated using confocal microscopy imaging of cellular $Ca^{2+}$ fluctuations in living cells, though other imaging tools may be used. In two worked examples in which $Ca^{2+}$ dynamics were measured the present invention showed that increased $Ca^{2+}$ flux correlates with altered cell viability in human and mouse cells in culture and that increased $Ca^{2+}$ flux predisposes to arrhythmia in a cell-based model of ionic handling, see FIG. 14.

Cellular data can be generated from $Ca^{2+}$ probe studies such as fluorescent probe studies using cardiac cells such as, for example, HL-1 cardiac cells.

HL-1 cardiomyocytes are an immortalised cardiac cell lineage that retains contractile, proteomic and molecular characteristics of adult cardiomyocytes. They are a robust, fast-growing and phenotypically stable cell line that exhibit spontaneous and synchronous beating when cultured into monolayers. Currently, they are the only cardiomyocyte derived lineage amenable to high-efficiency transfection of heterologous recombinant proteins using conventional (ie. non-viral) transfection methodologies. At high density and on suitable matrices such as a gelatin-fibronectin matrix they form electrically-coupled monolayers (a beating syncytium) that represents a robust model of cardiac cell rhythmicity, synchronicity and contractility.

As an example, the cells are cultured in Claycomb medium (SAFC Biosciences) containing foetal calf serum (10% (v/v)), glutamine (2 mM), norepinephrine (0.1 mM), penicillin (100 units/mL) and streptomycin (100 µg/mL) on plasticware pre-coated (24 hours) with gelatin-fibronectin (GFN; containing 0.2% (w/v) gelatin/10 µg/ml fibronectin (from bovine skin, Sigma)). For routine phenotypic characterisation, cells are fed daily (via complete media exchange) and are passaged weekly (split 1:3 into fresh, GFN coated plasticware). Lower split densities are associated with loss of phenotype. For imaging, cell seeding density is adjusted proportionally to surface area. Cells are cultured to very high densities (approximately 500 to 1000 cells/$mm^2$) on glass bottomed chambers (Mattek Corp., USA) such that they form electrically coupled monolayers (a beating syncytium). The cells may or may not be physically contractile at this point. Physical contraction is not a predictor of inter- and intra-cellular ion handling and data from both population types are entirely equivalent.

As a specific example, for cell imaging and data acquisition, the monolayers are loaded with 4.7 µM fluo4-AM (Invitrogen) at 30-37° C. for 90 minutes under a 200 µl volume of unsupplemented Claycomb medium. After this time, chambers are flooded with 1.2 ml Claycomb medium (containing norepinephrine (0.1 mM)) and returned to 37° for 20 minutes prior to imaging. Fields of view (FOV) containing at least 20 cells and exhibiting clearly detectable fluorescence levels (typically >20 arbitrary fluorescence units ((256 bit scaling) at a photomultiplier tube voltage of approximately 700V) are excited using a 488 nm Argon laser (20% power source). Data is acquired via a 40× or 63× (>1.3NA) oil-immersion objective lens using a Leica SP5 acoutso-optic beam splitter (AOBS) confocal microscope controlled with Leica LAS software. Data is acquired at 100 ms intervals in uni-directional scan mode using four-dimensional imaging (XYZT; three physical dimensions (X, Y and Z) and time (T)), at a camera resolution of 512×512 pixels or better. Raw (image) data is saved as *.lif files and are archived in date ordered format on external hard drives or digital tape (DAT).

Image data is obtained from cellular regions of interest (ROI, typically 50 µm$^2$) using the 'Quantify'→'Tools'→'Stack Profile' functionality of LAS software. Although, any image analysis software with a plug-in compatible with LAS (NIH's ImageJ, Imaris' Bitplane, Improvision's Velocity) can be used to obtain data from these files. The image data obtained are multi-column data (time versus fluorescence intensity for each ROI) and are generated using the 'Report' function of LAS. The image data are saved in a Microsoft Excel compatible format (default save name is 'Chart0') and just one of these files is generated for the report. The image data in this format are imported into SALVO.

The SALVO method and system is looking for transient peaks in the ROIs. A transient peaks is defined herein as the intensity versus time trace going from a valley to a peak to a valley and which is clearly definable, over a predetermined threshold and discernable above background noise. In the example of fluorescent $Ca^{2+}$ probe studies described above a transient peaks represents $Ca^{2+}$ release followed by $Ca^{2+}$ sequestration.

Figure 1:
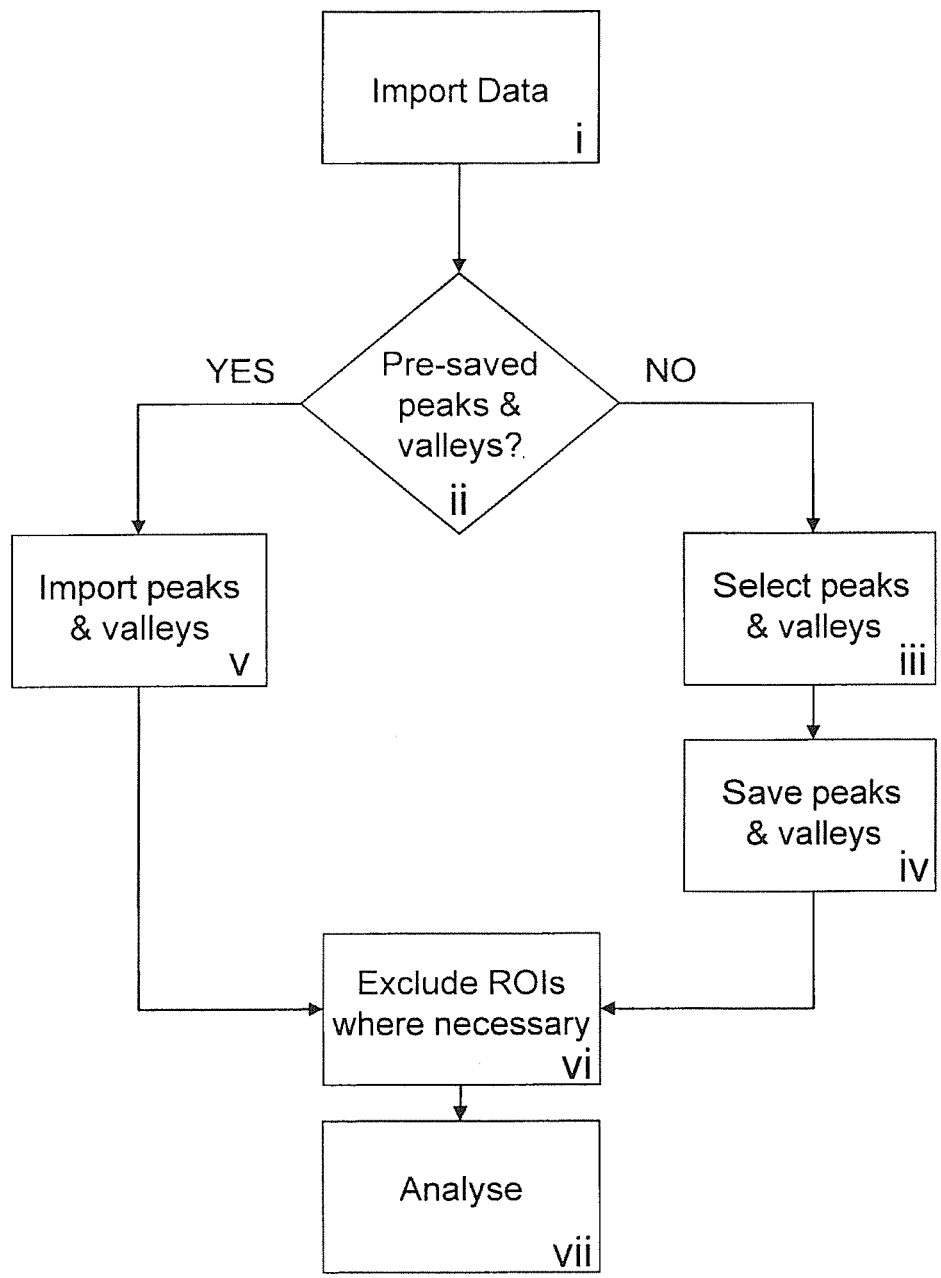
FIG. 1 is a flow chart showing the steps of the analysis performed by the method and system according to the present invention.
Figure 8:
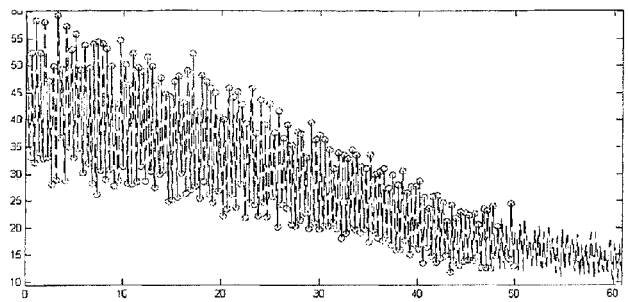
FIG. 8a shows raw trace data with peaks detected by the auto-detect model of FIG. 2.
FIGS. 8b to 8d show raw trace data with peaks detected by the threshold-detect model of FIG. 3, with different peak and valley cut off thresholds.
Figure 8:
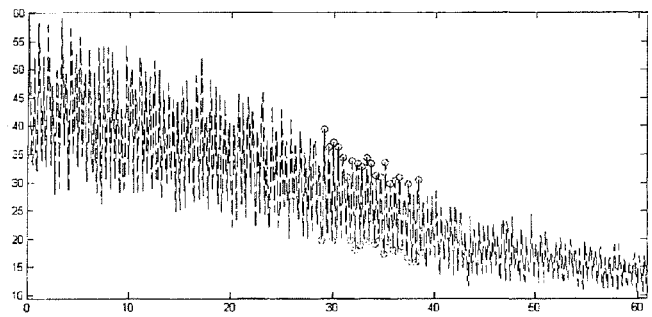
Figure 8:
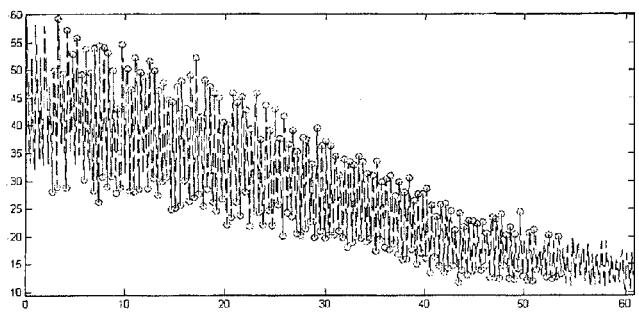
Figure 8:
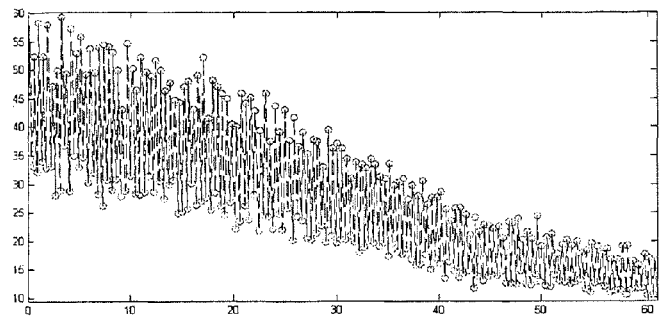

The flow chart of FIG. 1 shows the steps of the analysis performed by the SALVO method and system. Data is imported into SALVO [step i of FIG. 1]. This data may be raw image data (intensity, versus time for each ROI), imported as described above or from another source. The imported raw data may have previously been assessed for peaks and valleys using the SAVLO system. If this data (intensity of peak or valley versus time of peak or valley for a set of pre-saved peak data points and valley data points for each ROI) exists, it can be imported into the SALVO system directly instead of the user having to detect the peaks and valleys anew [step v via step ii of FIG. 1]. Where the data is raw image data, for each ROI, SALVO facilitates selection of peak data points and valley data points [step iii via step ii of FIG. 1], for example manually by the user and/or by a peak and valley selection model implemented in SALVO, which model may optionally require some user input. The peak and valley selection models include the auto-detect model described with reference to FIG. 2 below or the threshold-detect model described with reference to FIG. 3 below. The user may manually select the peak points by visually analysing a graph of the image data (intensity versus time). Optionally, where the auto-detect or threshold detect models are used to detect peak and valley points the results of these models, comprising a displayed data trace with the selected peaks and valleys marked on it (eg. as shown in FIG. 8), can be observed visually by the user and the user may then make any appropriate manual corrections to the peaks and valley selected by the models.

The peak points and valley points (intensity of peak or valley versus time of peak or valley) selected at step iii of FIG. 1 are then saved [step iv of FIG. 1] for each ROI. The raw data plus the saved [step iv of FIG. 1] or pre-saved [step v of FIG. 1] peak points and valley points are then analysed [step vi and vii of FIG. 1], as is described below in relation to FIG. 4.

SALVO uses two different models for detecting peaks and valleys in the time versus intensity (eg. fluorescence) raw image data imported into SALVO, which hereafter is referred to as the raw trace data. The user of SALVO can select which of these models to use for each ROI. The first is auto-detect and the second is threshold detect. Alternatively, the user can opt to manually select the peaks and valleys in the raw trace data and this option is sometimes preferred where there are a low number of transient events, and in particular where there are only one or two transient peaks per ROI. FIGS. 8a to 8d show example raw data traces with the detected peaks and valleys marked thereon. FIG. 8a shows the example trace, with peaks and valleys marked on it as identified by the auto-detect model. In most cases the auto-detect model is the best one to use, however, in some cases, for example, when there is a significant overall slope of the raw trace data, then user interaction within the threshold detect model may result in a better selection of peaks and valleys. Sometimes the auto-detect model can miss peaks and valleys towards the tail end of the raw trace. FIG. 8b shows the example trace, with peaks and valleys marked on it as identified by the threshold-detect model, with default thresholds peak=2 and valley=2. The peak thresholds are reciprocal indices. Thus, for example a threshold of 2 means that the potential peaks with an amplitude of greater than 50% of the maximum data trace amplitude will be detected. FIGS. 8c and 8d illustrate how user interaction with the threshold-detect model can change the outcome of the peak valley selection. In FIG. 8c, the user has selected the thresholds peak=3 and valley=3 and in FIG. 8d, the user has selected the thresholds peak=4 and valley=4 and in this latter case all peaks and valleys are successfully located.

The auto-detect model of selecting peaks and valleys attempts to automatically detect all valid peaks and valleys in the raw trace data. The stepwise method of the auto-detect model is set out below in relation to FIG. 2.

Figure 2:
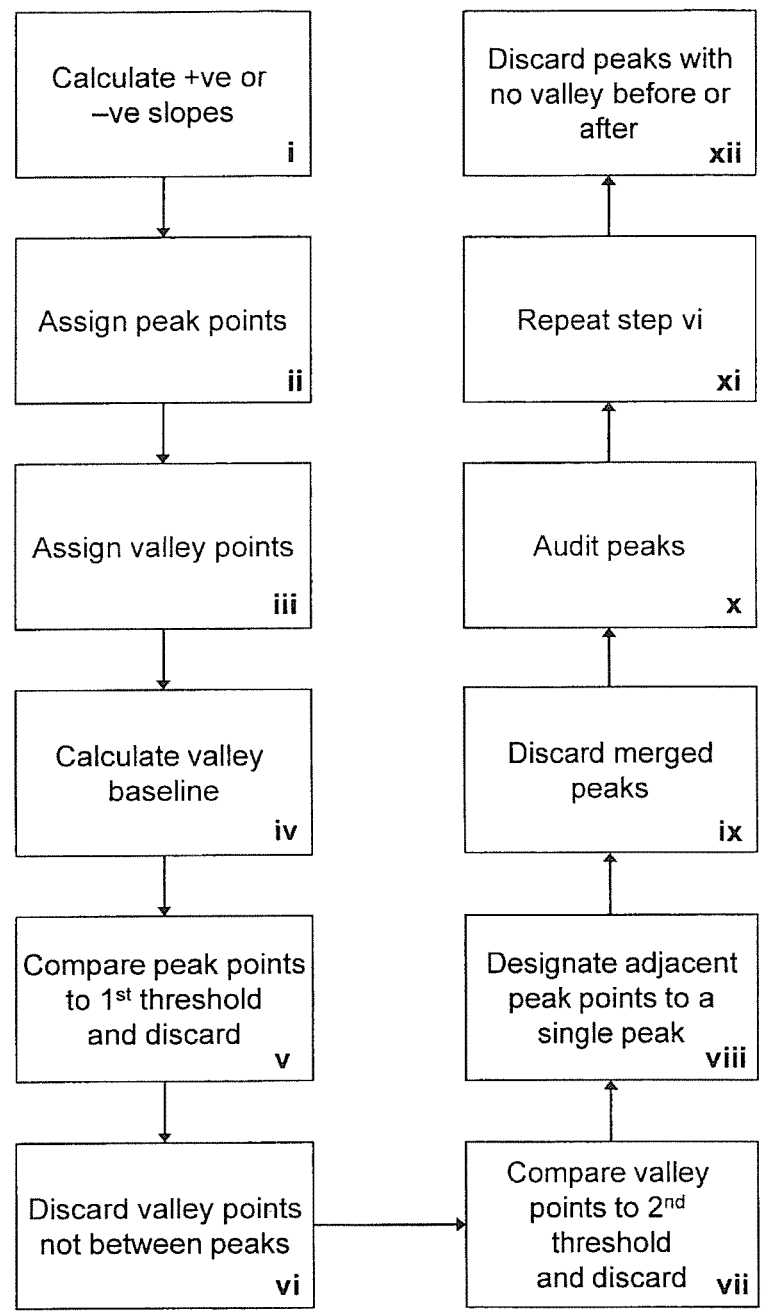
FIG. 2 is a flow chart showing the steps used to select peaks and valleys in the auto-detect model used in the 'Select peaks and valleys' step of FIG. 1.

All of the individual slopes between each data point in the trace data are assessed to determine whether they are positive or negative [step i of FIG. 2]. Then, for each data point, the data point is assigned as a potential peak point where the slope before the data point (in time) is positive and the slope after the data point (in time) is negative and otherwise is discarded as a potential peak point [step ii of FIG. 2]. Then for each data point, the data point is assigned as a potential valley point where the slope before the data point is negative and the slope after the data point is positive and otherwise is discarded as a potential valley point [step iii of FIG. 2]. A baseline intensity is then calculated as being the mean of the intensity of all of the data points assigned as potential valley points in step iii of FIG. 2 [step iv of FIG. 2]. Then, for each potential peak, the intensity of the potential peak is compared to a first threshold, which first threshold is set below the baseline intensity, preferably between 10% and 30%, and in particular 20% below the baseline. The percentage is selected based on experimental verification. Where the intensity of the potential peak is less than the first threshold, the potential peak is discarded as a potential peak point [step v of FIG. 2] for the following method steps. Then for each potential valley point, the valley point is discarded as a valley point, for the following method steps, where it does not have a potential peak point before or after it (in time), ie. it does not have a potential peak point between it and the previous valley or a potential peak point between it and the next valley [step vi of FIG. 2]. Then, for each potential valley, the intensity of the potential valley is compared to a second threshold, which second threshold is set above the baseline intensity, preferably between 70% and 90%, and in particular 80% above the baseline. Where the intensity of the potential valley is greater than the second threshold, the potential valley is discarded as a potential valley point [step vii of FIG. 2] for the following method steps. This identifies potential peak points and valley points. However, a peak or valley may be represented by more than one potential peak point or valley point, respectively.

Figure 10:
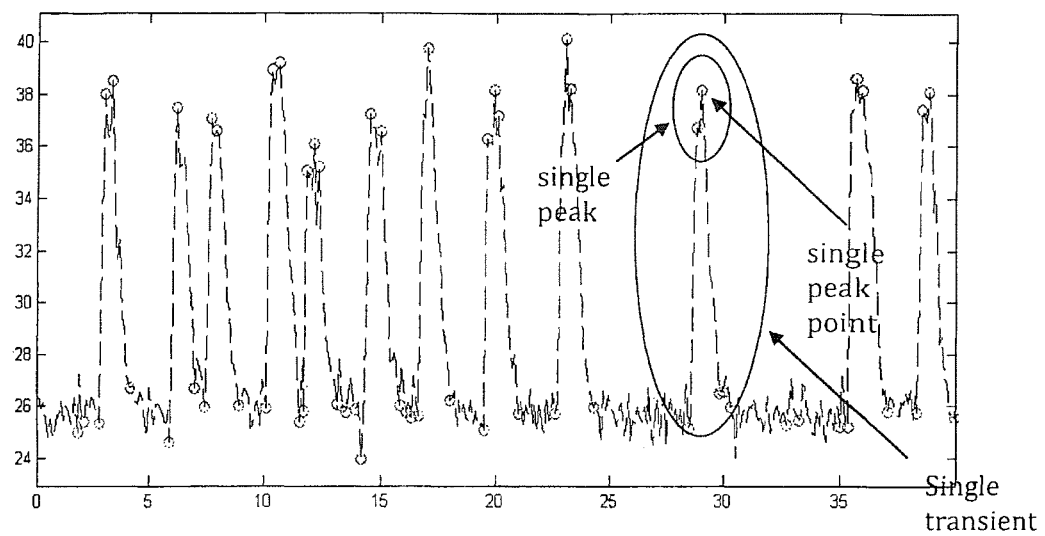
FIG. 10 shows raw trace data illustrating how more than one peak data point can represent a transient.

For each potential peak point, where the peak point is one of a plurality of potential peak points, that are between two potential valley points, ie. there are no potential valley points between the plurality of potential peak points, the plurality of potential peak points are designated as a single potential peak for the following method steps [step viii of FIG. 2]. FIG. 10 illustrates how a single peak, representing a single transient can be represented by more than one peak point.

Then any potential peaks are removed that appear to be merged, by calculating a third threshold. To do this the time at which each peak occurred is considered. If there is more than one potential peak point representing the peak then the mean of the times for each such peak point is taken to be the time that the peak occurred for the purposes of the calculation of the third threshold. Then the distance (in time) between the potential peak points making up the peak and the time the peak occurred (as calculated above) is calculated and a mean of these difference is calculated. Then to determine whether a peak that is represented by more than one point is a split peak (ie. two transient peaks that have run together) or whether it is a valid peak (ie. representing a single transient), the spread of the peak is calculated. The spread is the distance (in time) between the first and last points of the peak. The third threshold is then set at between 60% and 40%, preferably 50% of the calculated mean distance. Then any potential peak which has a spread greater than the third threshold are discarded as potential peaks in the following method steps [step ix of FIG. 2].

Merged peaks are removed so that they do not adversely affect transient calculations. However, removing them in this way does affect the synchrony and rate calculations. An alternative, is to mark merged peaks as abortive transient peaks, which are then included in the synchrony and rate calculations described below, but are not included in transient specific calculations, such as height, length, etc.

Figure 11:
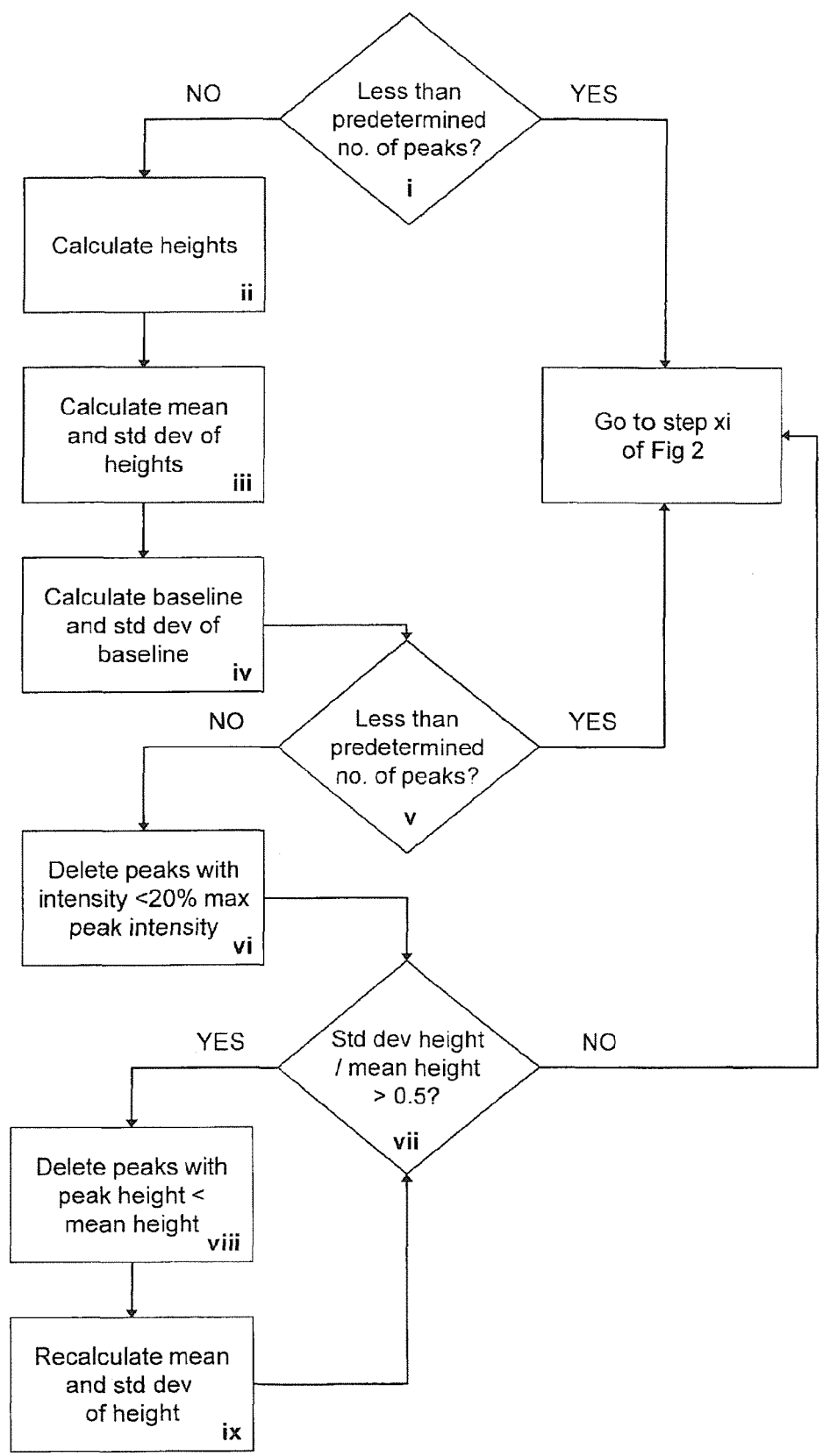
FIG. 11 is a flow chart showing the steps used in the 'Audit peaks' step of FIG. 2.

An audit peak step [step x of FIG. 2] is then carried out, in accordance with FIG. 11 in order to remove more of the peak points that represent background noise. The audit peak step is a mixture of checks to reduce the standard deviation of the peak heights and tests to determine whether or not the ROI should undergo deletions of peak points. First, if there are less than a predetermined number of peaks in the ROI, for example, the predetermined number may be between 8 and 13, preferably 11, then the model skips to step xi of FIG. 2 [step i of FIG. 11]. Otherwise, the heights of all of the peaks are calculated using the first peak point of each peak (ie. if there are two or more peak points representing a peak, the first one in time is chosen for this calculation) [step ii of FIG. 11]. The mean and standard deviation of the heights is then calculated [step iii of FIG. 11]. The baseline is calculated (mean intensity of the valleys) and the standard deviation of the valleys (intensity) [step iv of FIG. 11]. Then if:

(mean height+std dev of heights)/(baseline+std dev of baseline)<0.5 skip to step xi of FIG. 2 [Step v of FIG. 11]. Then any peak with an intensity<20% of the maximum peak intensity (with the maximum peak intensity based on the intensity of the first peak points) is deleted [step vi of FIG. 11].

Then if:

(std dev of heights)/(mean height)>0.5[step vii of FIG. 11]

go to step viii of FIG. 11 and otherwise go to step xi of FIG. 2.

At step viii of FIG. 11, for every peak if the height of the peak<mean height, delete the peak [step viii of FIG. 11] and recalculate the mean heights and standard deviation based on the remaining peaks [step ix of FIG. 11] then go back to step vii of FIG. 11.

At step xi of FIG. 2, step vi is repeated [step xi of FIG. 2].

Finally, any potential peaks without a potential valley either before it or after it (in time), are discarded as potential peaks in the following method steps [step xii of FIG. 2]. The remaining, potential peaks and potential valleys are the peaks and valleys selected by the auto-detect model of FIG. 2.

The stepwise method of the threshold-detect model is set out below in relation to FIG. 3.

Figure 3:
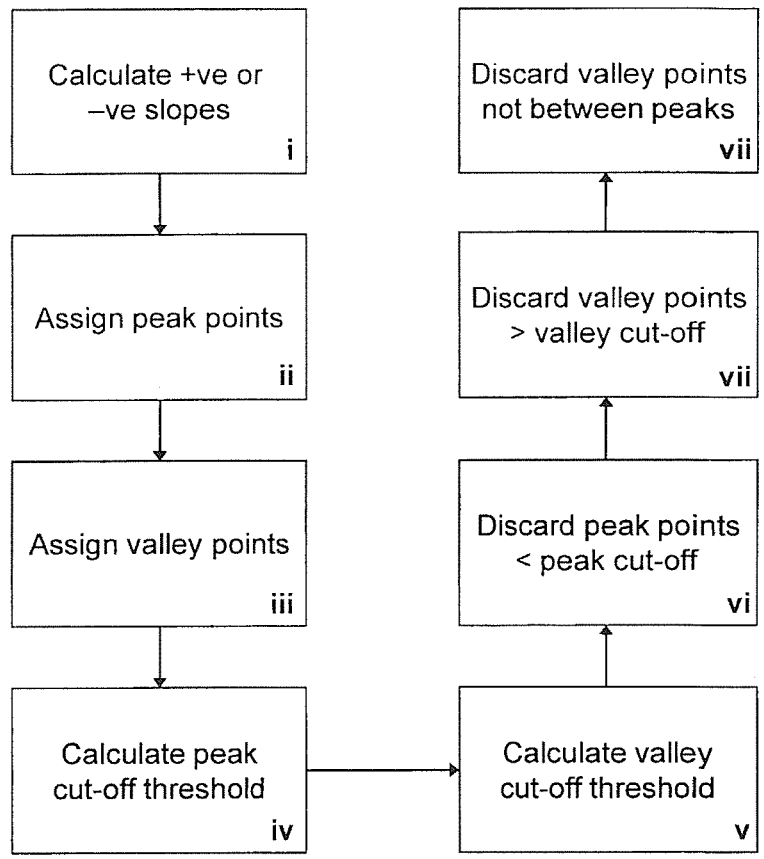
FIG. 3 is a flow chart showing the steps used to select peaks and valleys in the threshold-detect model used in the 'Select peaks and valleys' step of FIG. 1.

Steps i to iii of FIG. 3 are the same as steps i to iii of FIG. 2 to make an initial selection of potential peak points and potential valley points. A peak cut-off threshold is then calculated [step iv of FIG. 3], based on a fourth threshold value supplied by the user of SALVO, based on the user's observation of the trace as follows:

Peak cut-off threshold=maximum peak intensity/ fourth threshold.

The default value for the fourth threshold is 2 and the user determines the changes in the default threshold by eye. If too much noise is included at the default threshold, the fourth threshold gets lowered towards 1 and if too many peaks are missing at the default threshold, the fourth threshold is moved to be >2. The user may repeat this several times, choosing different thresholds, until the user is happy with the peak point selection.

A valley cut-off threshold is then calculated [step v of FIG. 3], based on a fifth threshold value supplied by the user of SALVO, as follows:

Valley cut-off threshold=minimum valley intensity/ fifth threshold.

Again the default value for the fifth threshold is 2 and the user determines the changes in the default threshold by eye. The fourth threshold gets lowered towards 1 or raised above 2 based on which valleys have been deleted. The user may repeat this several times, choosing different thresholds, until the user is satisfied that the valley point selection accurately describes the data traces.

Then all potential peak points with an intensity less than the peak cut-off threshold are discarded as potential peak points for the following method steps [step vi of FIG. 3] and all potential valley points with an intensity greater than the valley cut-off threshold are discarded as potential valley points for the following method steps [step vii of FIG. 3]. Then for each potential valley point, the potential valley point is discarded, for the following method steps, where it does not have a potential peak point before or after it, ie. it does not have a potential peak point between it and the previous valley or a potential peak point between it and the next valley [step viii of FIG. 3]. The remaining, potential peak points and potential valley points are the peaks and valleys selected by the threshold-detect model of FIG. 3.

The user can manually alter the peak points and valley points at any time.

Figure 9:
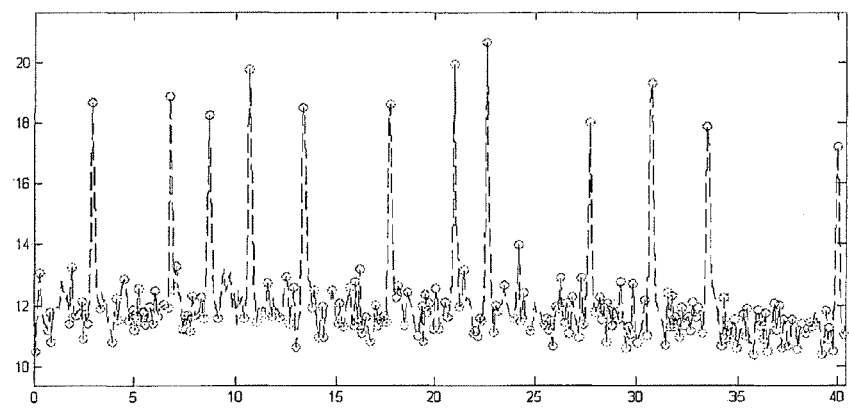
FIGS. 9a and 9b show raw trace data illustrating the manual removal of peaks by a user setting a threshold.
Figure 9:
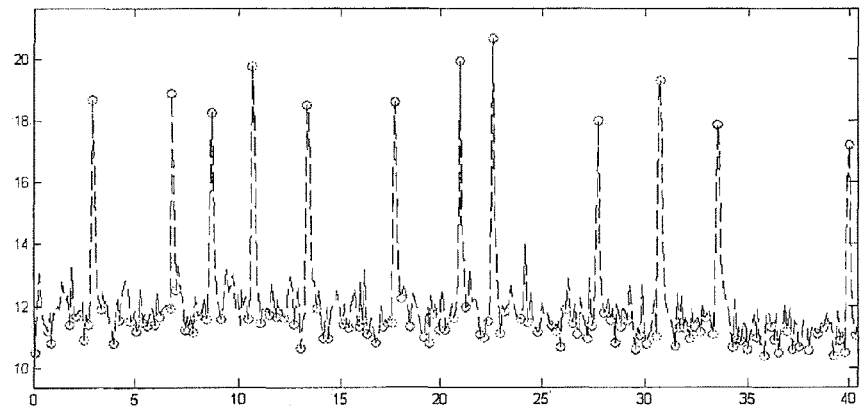

In some instances the auto-detect model of FIG. 2 and threshold detect model of FIG. 3 cannot discriminate between valid peak points and peaks of noise. Where this occurs, it is suggested that a further step is included, in which the user deletes all potential peak points under an intensity threshold. This process is illustrated in FIGS. 9a and 9b. FIG. 9a shows the peak and valley selection as identified by the auto-detect model. The user observes the results of the auto-detect model, as shown in FIG. 9a and based on this observation chooses a threshold under which all peaks should be deleted, for example, because they are classed as noise. In the example of FIG. 9a, where the user selects a threshold of 16, the trace of FIG. 9b is the result.

Figure 6:
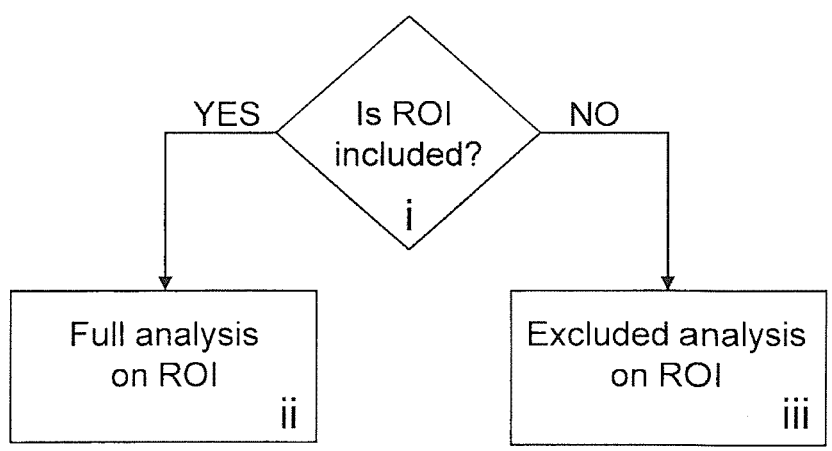
FIG. 6 is a flow chart showing the steps used in the 'Analysis of included ROIs and excluded ROIs' step of FIG. 4.

Any ROIs that do not include transient peaks are excluded from the full analysis, as are any ROIs where it is difficult to distinguish between the transient peaks and the background noise [step vi of FIG. 1 and step i of FIG. 6]. The excluded ROIs are analysed differently from included ROIs, as described below.

The stepwise analysis of the data at step vii of FIG. 1 is described below in relation to FIG. 4.

Figure 4:
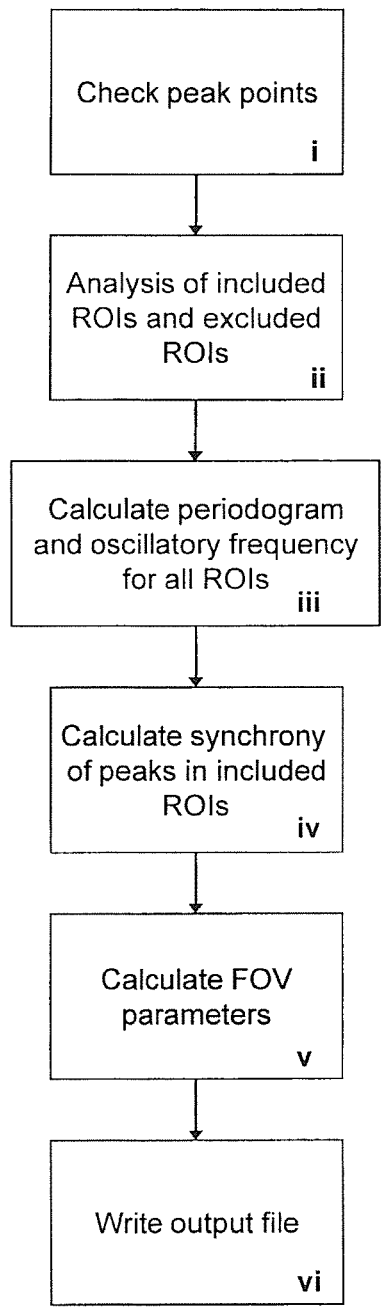
FIG. 4 is a flow chart showing the steps used in the 'Analyse' step of FIG. 1.

In FIG. 4 a final check is made of the peak points for all ROIs [step i of FIG. 4]. The final check comprises the following steps, as shown in FIG. 5.

Figure 5:
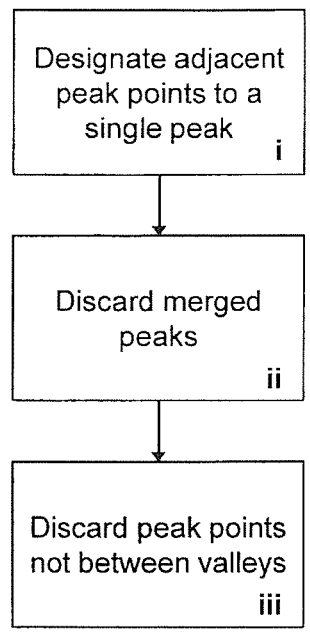
FIG. 5 is a flow chart showing the steps used in the 'Check peak points' step of FIG. 4.

For each potential peak point, where the peak point is one of a plurality of potential peak points, that are between two potential valley points, ie. there are no potential valley points between the plurality of potential peak points, the plurality of potential peak points are designated as a single potential peak point for the following method steps [step i of FIG. 5]. Then as is step ix of FIG. 2, any potential peak points are removed that appear to be merged [step ii of FIG. 5]. Finally, any potential peak points are removed that do not have a valley point both before and after it [step iii of FIG. 5].

Then a full analysis is performed on each ROI that is designated as 'included' and an excluded analysis is performed on each ROI that is designated as 'excluded [step ii of FIG. 4]. For included ROIs the full analysis is carried out and all of the parameters listed below in the left hand column of Table 1 below are calculated [step ii of FIG. 6]. All included ROIs are included in a synchrony calculation described below to calculate the synchrony of transient peaks from all the included ROIs in the FOV.

Any excluded ROIs are excluded from the full analysis, as are any ROIs where it is difficult to distinguish between the transient peaks and the background noise [step iii of FIG. 6]. The excluded ROIs are excluded from the synchrony calculation, described below. Only the SV, mean intensity, baseline parameters and oscillatory frequency, are calculated for excluded ROIs [i.e. SV (std dev), SV total, SV (variance), SV/s, SVm, ITN (roi total), ITN (total length), ITN (ave total), ITN (ave length), ITN (ave mag), ITN/s] and so excluded ROIs are excluded from all transient specific calculations.

The calculation of inter-transient noise ITN for an excluded ROI is shown in FIG. 12b, whereas the calculation of inter-transient noise ITN for an included ROI is shown in FIG. 12a.

A periodogram and an oscillatory frequency are then calculated for each ROI, whether they are included or not [step iii of FIG. 4]. A fast fourier transform is used to calculate the power and frequency that represents the periodogram for each ROI. The oscillatory frequency parameter (Table 1) is then designated as the value of the oscillatory frequency with the maximum power.

A strict approach is used for the synchrony calculation in that for two peaks to be classed as synchronous they have to occur at the same time. Where a peak is represented by two or more data points, the time that the peak occurs is classed as any time between the first data point and the last data point for that peak. The synchrony between the peaks of the included ROIs is calculated [step iv of FIG. 4] as described below in relation to FIG. 7.

Figure 7:
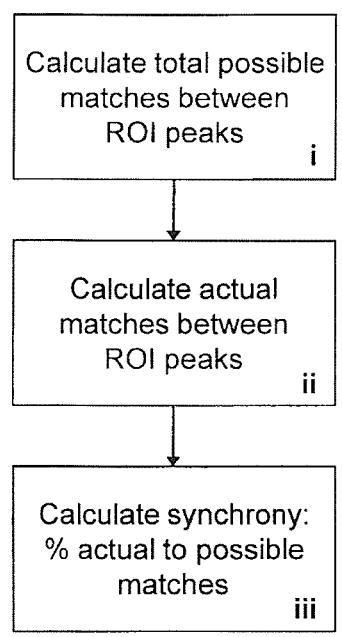
FIG. 7 is a flow chart showing the steps used in the 'Calculate synchrony of peaks in included ROIs' step of FIG. 4.

The total number of possible matches (pairwise) between ROI peaks is calculated [step i of FIG. 7] based on the ROI with the maximum number of peaks. Two peaks in different ROIs are designated as a matching pair where they occur at the same time, as is described above. For example, if the ROI with a maximum number of peaks has 60 peaks, then the total number of possible matches would be if all ROIs had 60 peaks and all 60 peaks in each ROI occurred at exactly the same times. This would be calculated as:

Total possible matches=number of combinations× maximum number of peaks.

Thus, if there are 20 included ROIs, RO1 will be compared with 19 others, RO2 to 18 others, and RO19 will be compared to 1 other. Thus, the number of combinations is 19+18+ . . . +1.

Then the actual number of matched pairs of peaks are calculated by iterating through each included ROI and for each included ROI, iterating through each peak of the ROI and for each peak counting how many times that peak matches a peak in the included ROIs iterated after the current one [step ii of FIG. 7]. The number of matched peak pairs, for each peak of each ROI are then summed to calculate the number of counted matches. The percentage synchrony is then calculated [step iii of FIG. 7] as:

(Number of counted matches/Total possible matches)×100

The other parameters listed in the right hand column of Table 1 are calculated for the FOV [step v of FIG. 4]. Then the output file is written [step vi of FIG. 4].

In the example where SALVO is used for investigating the $Ca^{2+}$ handling basis of intercellular synchrony it returns 25 parameters, as shown in the left hand column of Table 1, describing signal fluxes in individual ROIs and 28 parameters, as shown in the right hand column of Table 1, describing mean data within a microscopic field of view (FOV). For example, each ROI may correspond to a single cell and the FOV may correspond to 10 to 20 cells.

Figure 13:
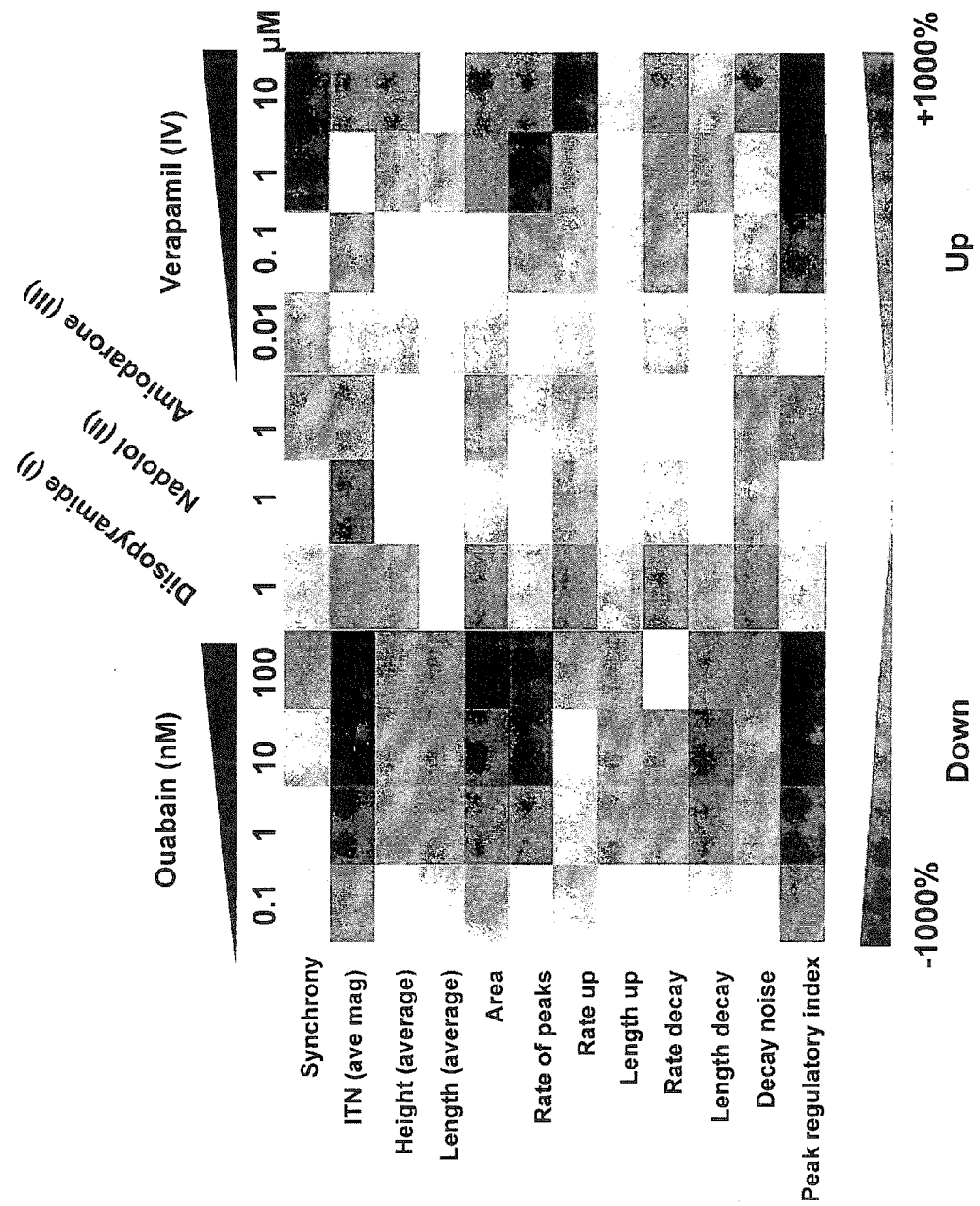
FIG. 13 is a conventional heat map showing the effects of a number of drugs or pharmacologies (Ouabain, Diisopyramide (II), Nadolol (I), Amiodarone (III), & Verapamil (IV)) on calcium handling in cardiac tissue as measured by inter-transient noise and a number of peak parameters.

As shown in experiments in which monolayers were exposed to the known arrhythmogen ouabain (FIG. 13), inter-transient signal data is inversely related to intercellular synchrony in the monolayer. Known anti-arrhythmics, particularly class I (diisopyramide) and class III (amiodarone) agents can reduce inter-transient noise (ITN) and this is linked to restoration, even an improvement of synchrony. The relative suppression of ITN, and the accompanying restoration of synchronous behaviour in the monolayer using these agents is also linked to profound normalisation of 'transient' Ca2+ parameters including peak height, length, area, rate and peak regularity index (FIG. 13). Data in FIG. 13 shows that the anti-arrhythmic potential of prospective cardiac pharmacologies could be screened using this model system. Also, the multi-parametric nature of the output may allow the mechanistic basis of drug action to be determined.

Although the invention has been exemplified using a monolayer of immortalised cardiac cells other cells may be used to work the invention such as stem cell derived cells, particularly stem cell derived $Ca^{2+}$ handling cells such as muscle cells and ideally cardiac cells.

TABLE 1

| For each ROI | For the FOV (means) |
|---|---|
| SV (total) | Number of ROIs Included |
| SV (std dev) | Synchrony (as calculated wrt FIG. 7) |
| SV (variance) | Sampling rate |
| SV/s | Total Time |
| SVm | Included SV |
| ITN (roi total) | Excluded SV |
| ITN (total length) | Included SV/s |
| ITN (ave total) | Excluded SV/s |
| ITN (ave length) | Included SVm |
| ITN (ave mag) | Excluded SVm |
| ITN/s | ITN (roi total) |
| Baseline | ITN (tot length) |
| Mean Intensity of ROI | ITN (ave total) |
| Height (average) | ITN (ave length) |
| Length (average) | ITN (ave mag) |
| Area (average) | ITN/s |
| Number of Peaks | Baseline (mean of ROI baselines) |
| Rate of peaks | Mean Intensity of FOV |
| Rate Up | Height |
| Length Up | Length |
| Rate Decay | Area |
| Length Decay | Rate |
| Slope (entire ROI) | Rate Up |
| Peak RegIndex | Length Up |

TABLE 1-continued

| For each ROI | For the FOV (means) |
| --- | --- |
| Oscillatory Frequency of ROI | Rate Decay |
| | Length Decay |
| | Peak RegIndex |
| | Osc Freq |

Thus, the results file contains 25 parameters describing signal fluxes in individual ROIs (each representing a single cell) and 28 parameters (mean data) for multiple cells (typically 10-20 per FOV).

An explanation of the measurements of Table 1 are provided in Table 2.

TABLE 2

| | | |
| --- | --- | --- |
| SV | Signal variability | Sum of the absolute difference (intensity) between each point. |
| SV(dev) | Std dev of SV | |
| SV (var) | Variance of SV | |
| SV/s | | SV/(number seconds data collected for) |
| SVm | | SV/(mean intensity) |
| ITN (total roi) | Inter-transient noise | Calculated in the same way as SV but cutting out the transients. This is the total (sum) for the whole ROI |
| ITN (total length) | | Total amount of time that there was ITN for the whole ROI |
| ITN (ave total) | | Ave amount of ITN between each transient. |
| ITN (ave length) | | Ave length of time of ITN between each transient |
| ITN (ave mag) | | Ave height of the ITN (rather than summing them all up, what is the actual magnitude - ie how noisy) |
| Baseline | | Mean intensity of all valleys |
| Mean Int | Mean intensity | Mean intensity of whole ROI |
| Height | Transient Height | Average height of all of the transients for the ROI |
| Length | Transient Length | Average length of all of the transients for the ROI |
| Area | Transient Area | Average area of all of the transients for the ROI |
| Number of peaks | | That occurred within the time frame |
| Rate | Rate of peaks | This is in Hz. So that is number peak/second |
| Rate up | Rate of time transient takes to reach peak | A straight-line calculation of the slope from the starting valley point to the first peak point |
| Length up | Length of time transient takes to peak | The time the first peak point is minus the time of the starting valley |
| Rate decay | Rate of time transient takes to get back to valley | A straight-line calculation of the slope from the first peak point to the ending valley point. |
| Length decay | Length of time transient takes to get back to valley | The ending valley time minus the first peak point time. |
| Slope (entire ROI) | The slope of the whole ROI | Straight-line calculation of the slope between the first and last valley of the ROI. |
| Peak RegIndex | Peak regularity index | Currently the standard deviation of the distance between peaks (looking to normalise this however so is currently undergoing development) |

The skilled artisan will immediately appreciate that the method and system according to the above description can be readily implemented in software and in computing system environments and computing systems implementing such software. In one embodiment, a computing system environment is provided for analysing contractions or $Ca^{2+}$ transients in an in vitro sample of electrically coupled cells. As described, the method includes providing electrically coupled cells supported on a matrix and loading the cells with a detectable signal indicative of said contractions or $Ca^{2+}$ transients within one or more cells. An imager is provided for detecting said detectable signal and storing an image of said signal, which may be a microscope operatively linked to at least a processor, memory, and physical storage configured for receiving and storing images of the detectable signal.

In turn, a non-transient computer program product is provided which may be resident on one or more physical computing devices or available as a download. The computer program product is configured at least for receiving, storing, and analyzing data defining a data trace of one or more images for at least one region of interest (ROI). As discussed above, the ROI comprises a defined field of view of the imager for the sample of electrically coupled cells. The data trace defines a plurality of variations in the contractions or $Ca^{2+}$ transients within the one or more cells, detected over a predetermined time period. The computer program product, identifying portions of the data trace defining peaks which correspond to peaks in said contractions or $Ca^{2+}$ transients, selecting ROIs comprising at least one transient peak as included ROIs, and analysing the sections of the data trace which do not comprise contractions or $Ca^{2+}$ transients to provide a first set of parameters representing inter-transient noise for the or each included ROI. In one embodiment, the computer program product implements the multi-parametric analytical system and method for analysing dynamic phenomena references above by the acronym SALVO, and conducts the analyses and reports described in detail above.

In another embodiment, a computing system for analysing contractions or $Ca^{2+}$ transients in an in vitro sample of electrically coupled cells is provided. As discussed above, the system includes at least an imager for detecting a detectable signal from said electrically coupled cells and storing an image of said signal. The imager may be a microscope as explained above. Operatively linked to said imager, at least one computing device having a hardware platform having at least a processor, memory, and available storage is provided. A user interface allowing a user to control and interact with the system is provided. The user interface also allows displaying the data trace for at least one ROI to the user.

The system further includes a non-transient computer program product residing on one or more physical computing devices, configured at least for receiving, storing, and analysing data defining the data trace one or more images for at least one region of interest (ROI), which in turn comprises a defined field of view of said sample of electrically coupled cells. The data trace defines a plurality of variations in the contractions or $Ca^{2+}$ transients in one or more cells, detected and imaged over a predetermined time period.

As such, the skilled artisan will readily appreciate that by the present method and computing environments/systems implementing the method, it is possible to fully analyse dynamic phenomena in cells such as electrically coupled cell systems, in one non-limiting example as discussed above, contractions or $Ca^{2+}$ transients in cardiac cells supported in vitro on a suitable matrix. Moreover, the recited methods find ready application to detection and analysis of other phenomena, such as effects of drugs or other external stimuli on cells. Of course, the skilled artisan will also readily appreciate that other cell and non-cell (chemical and physical) systems, other imaging systems and other modes of data acquisition other than those described above can be analysed by SALVO provided they generate data in time.

The foregoing has been described in terms of specific embodiments, but one of ordinary skill in the art will recognize that additional embodiments are possible without departing from its teachings. This detailed description, therefore, and particularly the specific details of the exemplary embodiments disclosed, is given primarily for clarity of understanding, and no unnecessary limitations are to be implied, for modifications will become evident to those skilled in the art upon reading this disclosure and may be made without departing from the spirit or scope of the invention. Relatively apparent modifications, of course, include combining the various features of one or more figures with the features of one or more of the other figures, application of the described methods to different cell types, and the like.

The invention claimed is:

1. A system for analysing contractions or $Ca^{2+}$ transients in an in vitro sample of functionally-coupled cells, comprising:
    a matrix for supporting said cells;
    an imager for imaging said cells;
    a reagent for emitting at least one detectable signal representative of said contractions or Ca2+ transients;
    memory means for storing a data trace of said image for a least one region of interest (ROI) making up a measured field of view of said cells, wherein the data trace represents variations in said contractions or Ca2+ transients versus time;
    a non-transitory computer program product residing on at least one computing device including at least a processor, memory, and available storage, configured for investigating the data trace for the, or each, ROI to identify one or more first sections of the data trace comprising peaks in the trace which correspond to peaks in the contractions or Ca2+ transients;
    further wherein the computer program product is configured for selecting and analyzing ROIs including at least one transient peak as included ROIs; and
    further wherein the computer program product is configured also for selecting and analysing one or more second sections of the data trace which do not comprise contractions or Ca2+ transient peaks to generate a first set of parameters representing a signal variability (SV) of inter-transient noise (ITN) between the included ROIs, and analysing said one or more first data trace sections and said one or more second data trace sections to provide a more complete analysis of the variations in said contractions or Ca2+ transients versus time.

2. The system according to claim 1 wherein said cells are cardiac cells.

3. The system according to claim 2 wherein said cells are immortalised cardiac cells.

4. The system according to any one of claim 1 or 2 wherein said cells are provided as a monolayer.

5. The system according to claim 1 wherein said signal is a fluorescent molecule.

6. The system according to claim 1 wherein said imaging means is a confocal microscope.

7. The system according to claim 1 wherein said cells are cultured at a density of between approximately 500-1000 cells/mm$^2$.

8. The system according to claim 1 wherein the computer program product is configured also for analysing the data trace for the at least one ROI to generate a second set of parameters representing the data trace for that ROI.

9. The system according to claim 8 wherein the first and second sets of parameters each include a measure of signal variability.

10. The system according to claim 8 wherein the computer program product is configured also for analysing the transient peaks to generate a third set of parameters representing transient peaks for the included ROIs.

11. The system according to claim 10 wherein the computer program product is configured also for outputting parameters for the included ROIs separately.

12. The system according to claim 10 wherein the computer program product is configured also for generating at least one of:
    a set of parameters for a field of view representing inter-transient noise based on the first set of parameters; and
    a set of parameters for a field of view representing transient peaks based on the third set of parameters.

13. The system according to claim 12, wherein the set of parameters for the field of view representing transient peaks includes a measure of the synchrony between the transient peaks across the field of view based on the third set of parameters for the included of ROIs.

14. The system according to claim 13 wherein measure of synchrony is calculated by calculating an index of the total possible number of synchronised transient peaks across the field of view when compared with the actual number of synchronised transient peaks across the field of view.

15. The system according to claim 14, wherein the computer program product is configured also for identifying peaks which represent merged transient peaks for the purposes of calculating synchrony.

16. The system according to claim 13, wherein the computer program product is configured also for identifying peaks which represent merged transient peaks for the purposes of calculating synchrony.

17. The system according to claim 10, wherein the computer program product is configured also for discarding peaks which represent merged transient peaks for the purposes of analysing the transient peaks to generate the third set of parameters.

18. The system according to claim 8, wherein the computer program product is configured also for generating at least one of:
    a set of parameters for a field of view representing the data traces for included ROIs based on the second set of parameters;
    a set of parameters for a field of view representing the data traces for ROIs not designated as included ROIs based on the second set of parameters; and
    a set of parameters for a field of view representing the data traces for all the ROIs in the field of view based on the second set of parameters.

19. The system according to claim 8 wherein the second set of parameters includes an oscillatory frequency for the data trace.

20. The system according to any one of claim 1 or 8 wherein the computer program product is configured also for outputting parameters for the included ROIs separately.

21. The system according to claim 1 wherein the computer program product is configured also for displaying the data trace for the at least one ROI on a display screen operatively linked to the computing device, while the data trace for that ROI is investigated to identify the sections of the data trace comprising peaks in the trace which correspond to a transient event in the dynamic phenomena.

22. The system according to claim 21 wherein the computer program product is configured also for allowing a user observing the trace data to select transient peaks in the trace.

23. The system according to any one of claim 1 or 21 additionally comprising a user interface via which a user can interact with the system.

24. A method for analysing contractions or $Ca^{2+}$ transients in an in vitro sample of electrically coupled cells, comprising:
providing matrix supported cells wherein said cells are provided with a reagent providing a detectable signal indicative of Ca2+ transients within one or more of said cells;
imaging said Ca2+ transients;
storing a data trace of said imaged Ca2+ transients for a least one region of interest (ROI) making up a measured field of view of the sample, wherein the data trace represents variations in said contractions or Ca2+ transients versus time;
analyzing the data trace for said at least one ROI, to identify one or more first sections of the data trace comprising peaks in the trace which correspond to peaks in the contractions or Ca2+ transients;
selecting ROIs including at least one transient peak as included ROIs; and
selecting and analysing also one or more second sections of the data trace which do not comprise contractions or Ca2+ transient peaks to generate a first set of parameters representing a signal variability (SV) of inter-transient noise (ITN) between the included ROIs, and analysing said one or more first data trace sections and said one or more second data trace sections to provide a more complete analysis of the variations in said contractions or Ca2+ transients versus time.

25. The method according to claim 24, comprising exposing said cells to a test drug prior to the imaging to screen an effect of said test drug on said cells.

26. In a computing system environment, a method for analysing contractions or $Ca^{2+}$ transients in an in vitro sample of electrically coupled cells, comprising:
providing said electrically coupled cells supported on a matrix;
loading said cells with a reagent providing a detectable signal indicative of said contractions or $Ca^{2+}$ transients within one or more of said cells;
providing an imager for detecting said detectable signal and storing an image of said signal;
providing a non-transitory computer program product residing on one or more physical computing devices, said computer program product configured at least for receiving, storing, and analyzing data defining a data trace of said image for at least one region of interest (ROI), said at least one ROI comprising a defined field of view of said sample of electrically coupled cells and said data trace defining a plurality of variations in said contractions or $Ca^{2+}$ transients over a predetermined time period;
by the computer program product, identifying one or more first sections of the data trace defining peaks which correspond to peaks in said contractions or $Ca^{2+}$ transients, selecting ROIs including at least one transient peak as included ROIs, and also selecting and analysing one or more second sections of the data trace which do not comprise contractions or $Ca^{2+}$ transients to provide a first set of parameters representing a signal variability (SV) of inter-transient noise (ITN) between the included ROIs, and analysing said one or more first data trace sections and said one or more second data trace sections to provide a more complete analysis of the variations in said contractions or Ca2+ transients versus time.

27. The method of claim 26, wherein said imager is a microscope operatively linked to at least a processor, memory, and physical storage configured for receiving and storing said images.

28. The method of claim 26, further including, by the computer program product, analysing the data trace for the at least one ROI to generate and output a second set of parameters.

29. The method of claim 28, further including, by the computer program product, analysing the data trace for the at least one ROI to generate and output a third set of parameters.

30. The method of claim 29, further including, by the computer program product, generating and outputting at least one of:
a set of parameters for a measured field of view defining inter-transient noise based on the first set of parameters; and
a set of parameters for a measured field of view representing transient peaks based on the third set of parameters.

31. The method of claim 30, wherein the set of parameters for the field of view representing transient peaks includes a measure of synchrony between the transient peaks across the field of view based on the third set of parameters for the included ROIs.

32. The method of claim 31, including, by the computer program product, defining the measure of synchrony by calculating an index of a total possible number of synchronized transient peaks across the measured field of view when compared with the actual number of synchronised transient peaks across the measured field of view.

33. The method of claim 29, including, by the computer program product, discarding peaks defining merged transient peaks in generating the third set of parameters.

34. The method of claim 28, further including, by the computer program product, generating and outputting at least one of
a set of parameters for the measured field of view representing the data traces for included ROIs based on the second set of parameters;
a set of parameters for a measured field of view representing the data traces for ROIs not designated as included ROIs based on the second set of parameters; and
a set of parameters for a measured field of view representing the data traces for all ROIs in the measured field of view based on the second set of parameters.

* * * * *

UNITED STATES PATENT AND TRADEMARK OFFICE
CERTIFICATE OF CORRECTION

PATENT NO. : 8,666,676 B2  
APPLICATION NO. : 13/304962  
DATED : March 4, 2014  
INVENTOR(S) : George et al.

Page 1 of 1

It is certified that error appears in the above-identified patent and that said Letters Patent is hereby corrected as shown below:

In the Claims

Col. 19, lines 4-10

Please replace Claim 21 with:

21. The system according to claim 1 wherein the computer program product is configured also for displaying the data trace for the at least one ROI on a display screen operatively linked to the computing device, while the data trace for that ROI is investigated to identify the sections of the data trace comprising peaks in the trace which correspond to peaks in the contractions or Ca2+ transients.

Signed and Sealed this  
Eighth Day of July, 2014

Michelle K. Lee  
*Deputy Director of the United States Patent and Trademark Office*